(12) United States Patent
Kim

(10) Patent No.: US 11,229,550 B2
(45) Date of Patent: Jan. 25, 2022

(54) AQUEOUS HUMOUR DISCHARGE APPARATUS FOR GLAUCOMA PREVENTION

(71) Applicant: THE CATHOLIC UNIVERSITY OF KOREA INDUSTRY-ACADEMIC COOPERATION FOUNDATION, Seoul (KR)

(72) Inventor: Yong Chan Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 37 days.

(21) Appl. No.: 16/771,957

(22) PCT Filed: Dec. 12, 2018

(86) PCT No.: PCT/KR2018/015770
§ 371 (c)(1),
(2) Date: Jun. 11, 2020

(87) PCT Pub. No.: WO2019/156329
PCT Pub. Date: Aug. 15, 2019

(65) Prior Publication Data
US 2021/0186757 A1    Jun. 24, 2021

(30) Foreign Application Priority Data

Feb. 6, 2018    (KR) ........................ 10-2018-0014497

(51) Int. Cl.
*A61F 9/007*    (2006.01)
*A61M 27/00*    (2006.01)

(52) U.S. Cl.
CPC ......... *A61F 9/00781* (2013.01); *A61M 27/00* (2013.01); *A61M 2210/0612* (2013.01)

(58) Field of Classification Search
CPC .............. A61F 9/00781; A61M 27/00; A61M 2210/0612; A61M 27/002;
(Continued)

(56) References Cited

U.S. PATENT DOCUMENTS 9,168,172 B1 * 10/2015 Berdahl .............. A61F 9/00781
2006/0235367 A1 * 10/2006 Takashima .......... A61F 9/00781
604/541

(Continued)

FOREIGN PATENT DOCUMENTS

CN         104042401 A    9/2014
JP       2004-208898 A    7/2004
(Continued)

*Primary Examiner* — Andrew J Mensh
*Assistant Examiner* — Nhu Q. Tran
(74) *Attorney, Agent, or Firm* — Novick, Kim & Lee, PLLC; Sang Ho Lee; Hyun Woo Shin

(57) ABSTRACT

Provided is an aqueous humour discharge apparatus for glaucoma prevention. The aqueous humour discharge apparatus for glaucoma prevention includes: an aqueous humour discharge tube including a contact portion provided on one side and contacting the cornea of an eyeball, an exposed portion exposed not to contact the sclera of the eyeball and provided on the other side, and a channel formed between the contact portion and the exposed portion, to enable aqueous humour to flow therethrough; and a cover member arranged to surround the cornea and the sclera, the cover member including a contact hole formed on one surface that contacts the cornea, and contacted by the aqueous humour discharge tube, a discharge hole formed on the other surface located on the opposite side to the one surface and exposed to the outside, to discharge the aqueous humour, and a flow channel provided between the contact hole and the discharge hole to provide a discharge path of the aqueous humour.

4 Claims, 6 Drawing Sheets

(58) Field of Classification Search
CPC ............. A61M 2027/004; B29D 11/00; B29D 11/00076; G02C 7/04
See application file for complete search history.

(56) References Cited

U.S. PATENT DOCUMENTS

2007/0191863 A1\* 8/2007 De Juan, Jr. ............ A61F 11/00
606/108
2017/0095370 A1\* 4/2017 Velasquez ........... A61F 9/00781

FOREIGN PATENT DOCUMENTS

| KR | 10-2009-0005168 A | 1/2009 |
| KR | 10-2017-0028936 A | 3/2017 |
| KR | 10-1812246 B1 | 1/2018 |

\* cited by examiner

AQUEOUS HUMOUR DISCHARGE APPARATUS FOR GLAUCOMA PREVENTION

TECHNICAL FIELD

The present disclosure relates to aqueous humour discharge apparatuses for glaucoma prevention, and more particularly, to an aqueous humour discharge apparatus for glaucoma prevention having an improved structure such that aqueous humour may be smoothly discharged by preventing fibrotic capsulation due to a foreign body reaction when a discharge tube for treatment contacts a cornea to discharge aqueous humour, and infection may be suppressed.

BACKGROUND ART

An empty space between the cornea (iris) and the crystalline lens (lens) of our eye is filled with a liquid called 'aqueous humour'. When the tissues or cells of a human body age as the human body gets older, an aqueous humour outlet becomes gradually narrow, and accordingly the amount of aqueous humour created becomes larger than the amount of aqueous humour that is discharged, and thus the internal pressure of an eyeball (intraocular pressure) increases. Unfortunately, as the human body gets older, the aqueous humour outlet becomes further narrower. When this symptom continues, optic nerves that enter the eyes from the brain are first damaged and are gradually broken down to reach blindness, which is glaucoma.

The field of glaucoma has a basic goal of preventing damage to optic nerves by reducing an intraocular pressure. Because significantly effective eye drops have been developed for 20 years, a current blindness rate is significantly decreasing. Nevertheless, there are many patients who are not controlled by these eye drops, and surgical treatments are attempted on these patients.

A treatment that is currently widely used, among the surgical treatments, is a method using an Ahmed aqueous humour drainage mechanism A, as well illustrated in FIG. 1. This mechanism was developed in the 70s-80s and has reached a current mechanism through several modifications. However, because an aqueous humour outlet is formed in a posterior chamber of an eyeball tissue by passing through a conjunctiva space where the sclera is located, a foreign body reaction due to fiber cells is formed in the space as shown in FIG. 2, and causes fibrotic capsulation. Thus, aqueous humour is not smoothly discharged, leading to frequent occurrence of a problem of increasing the intraocular pressure.

DESCRIPTION OF EMBODIMENTS

Technical Problem

Provided is an aqueous humour discharge apparatus for glaucoma prevention that enables smooth discharge of aqueous humour by preventing fibrotic capsulation due to a foreign body reaction when a discharge tube for treatment contacts the cornea to discharge aqueous humour, suppresses infection, and improves the convenience of operators and users.

Solution to Problem

According to an aspect of the present disclosure, an aqueous humour discharge apparatus for glaucoma prevention includes: an aqueous humour discharge tube including a contact portion provided on one side, to contact the cornea of an eyeball, an exposed portion exposed so as not to contact the sclera of the eyeball and provided on the other side, and a channel formed between the contact portion and the exposed portion, to enable aqueous humour to flow; and a cover member arranged to surround the cornea and the sclera, the cover member including a contact hole formed on one side that contacts the cornea, and contacted by the aqueous humour discharge tube, a discharge hole formed on the other side located on the opposite side to the one side and exposed, to discharge the aqueous humour, and a flow channel provided between the contact hole and the discharge hole to provide a discharge path of the aqueous humour.

The cover member may be formed as a contact lens type by using a material as a material of a contact lens.

A flow path formation member may be included to form a flow channel of the cover member, may be formed together with the cover member according to an insert injection method when the cover member is molded, and may be detachably combined with the aqueous humour discharge tube.

The flow channel of the cover member may be configured to be arranged at a location of the sclera without being located on the cornea.

Advantageous Effects of Disclosure

An aqueous humour discharge apparatus for glaucoma prevention according to the present disclosure includes an aqueous humour discharge tube contacting the cornea to discharge aqueous humour but not contacting the sclera, and a cover member surrounding the cornea and the sclera and contacting the aqueous humour discharge tube in order to discharge the aqueous humour forwards, as described above, thereby enabling the aqueous humour to be discharged through the cover member while not in contact with the sclera. This addresses a conventional problem caused due to discharge of aqueous humour through the sclera, and thus it is possible to expect an excellent effect on the treatment or prevention of glaucoma through smooth discharge of aqueous humour and stabilization of the intraocular pressure.

According to an embodiment of the present disclosure, because the aqueous humour discharge tube is in contact with the cornea and at this state the cover member may be coupled with and separated from the aqueous humour discharge tube, the cover member may be smoothly replaced and treatment, such as disinfection, of the aqueous humour discharge tube may be smoothly performed, and thus the convenience of users and operators may improve.

DETAILED DESCRIPTION

An aqueous humour discharge apparatus for glaucoma prevention according to an embodiment of the present disclosure will now be described in detail with reference to the accompanying drawings.

Figure 1:
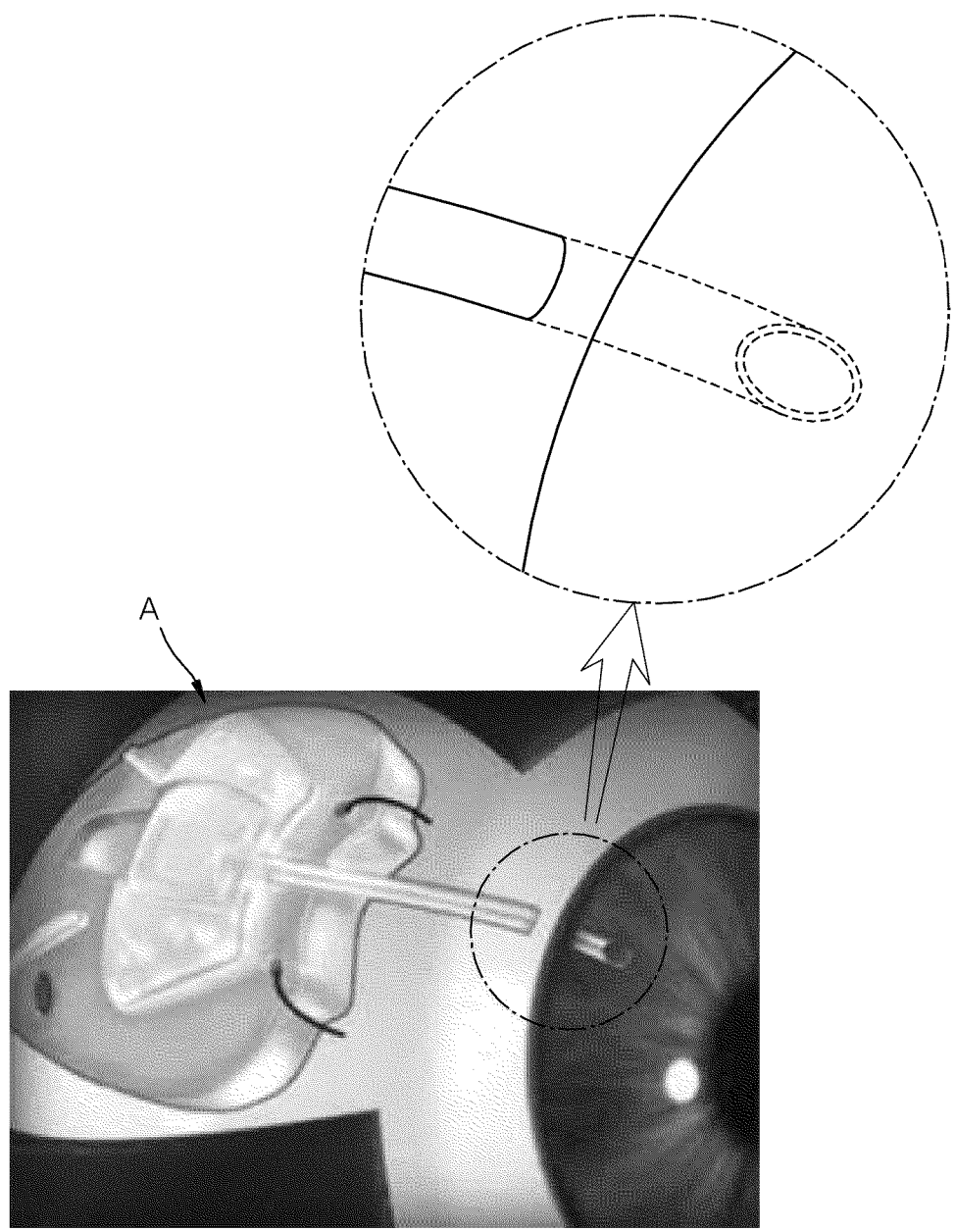
FIG. 1 is a view illustrating a use state of a conventional aqueous humour discharge apparatus for glaucoma prevention.
Figure 2:
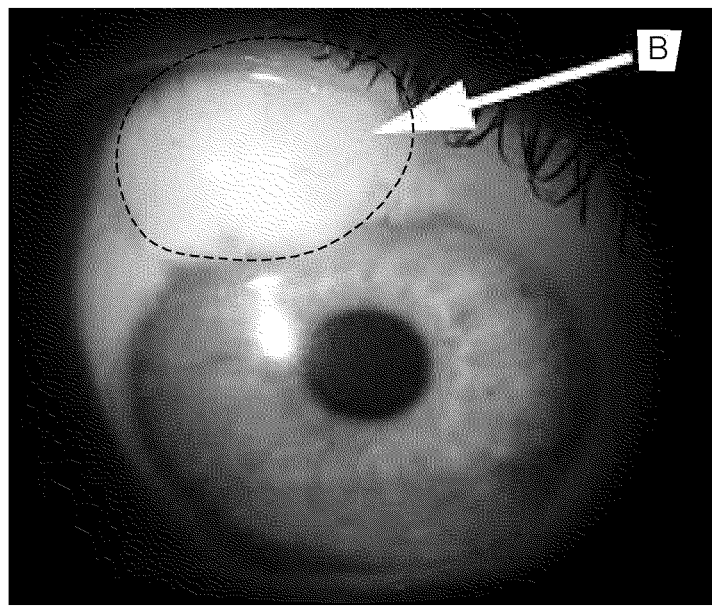
FIG. 2 is a photograph for explaining a conventional problem.
Figure 2:
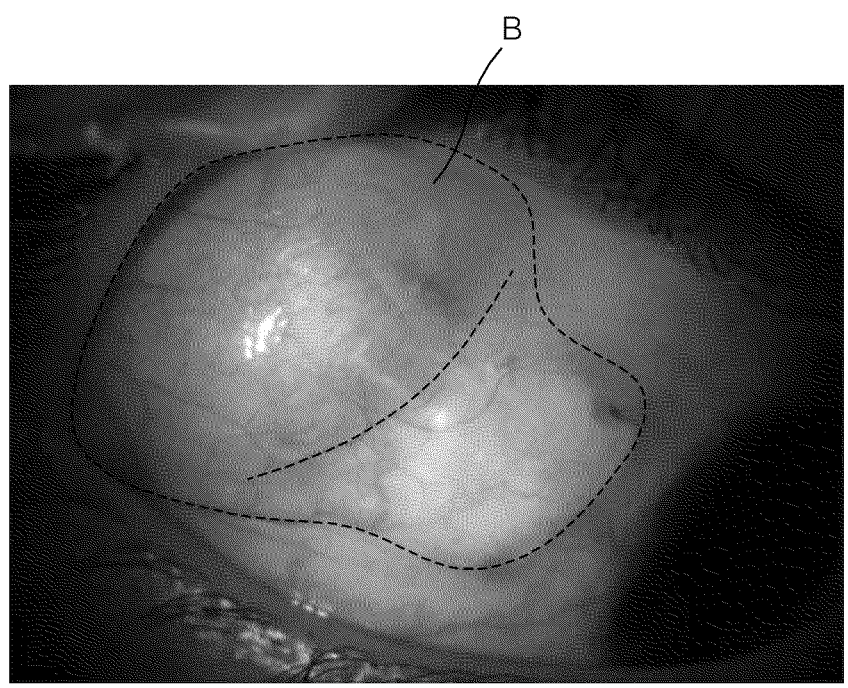
Figure 3:
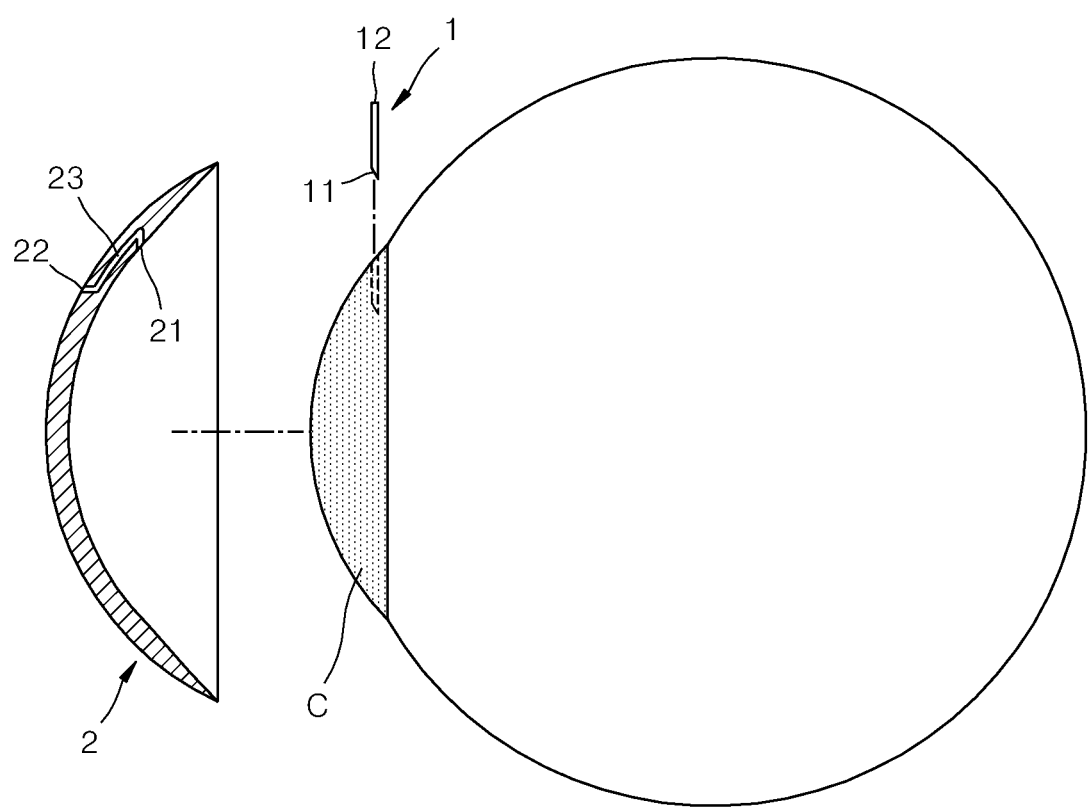
FIG. 3 is a cross-sectional view of an aqueous humour discharge apparatus for glaucoma prevention according to an embodiment of the present disclosure.
Figure 4:
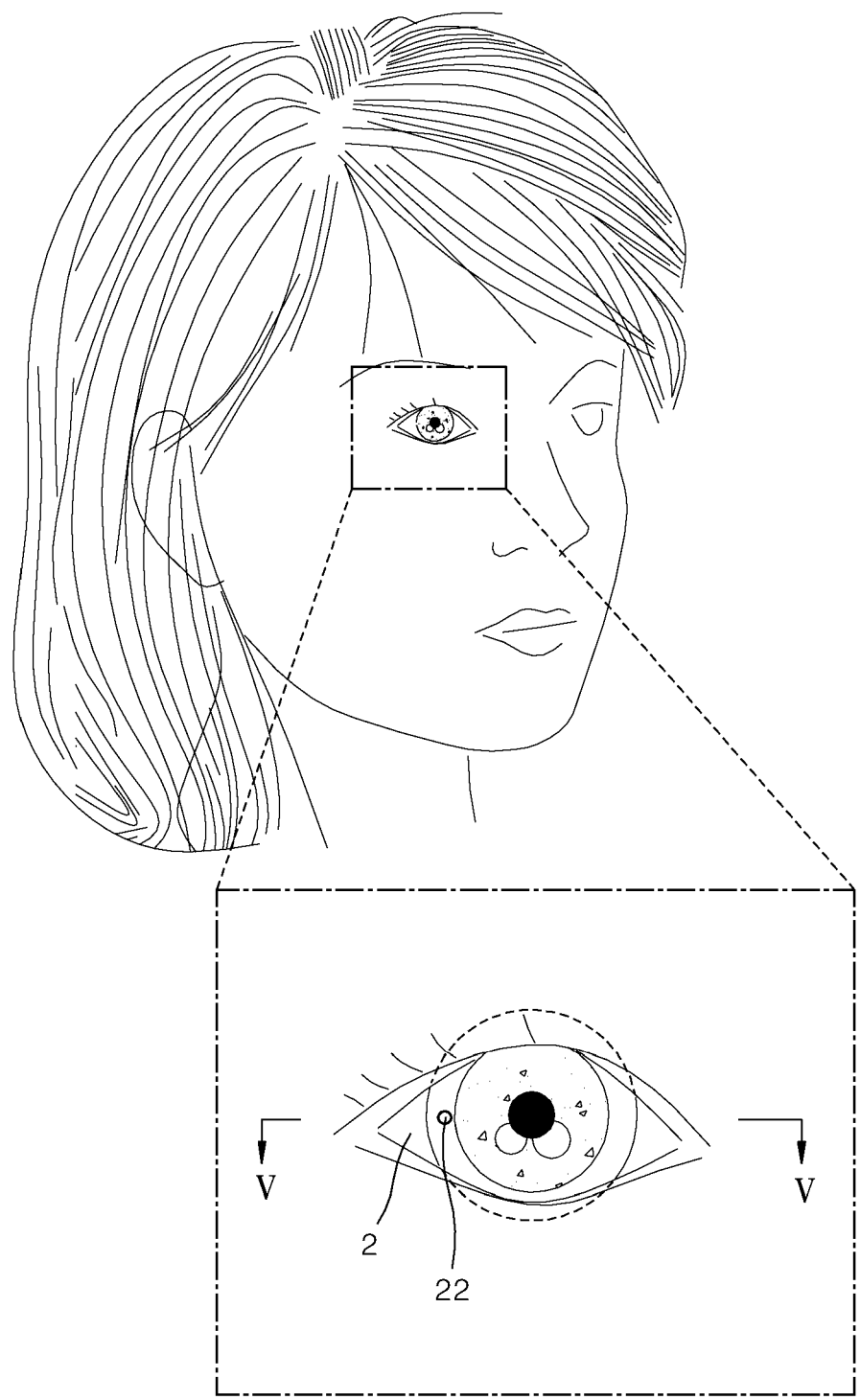
FIG. 4 is a view illustrating a use state according to an embodiment of the present disclosure.
Figure 5:
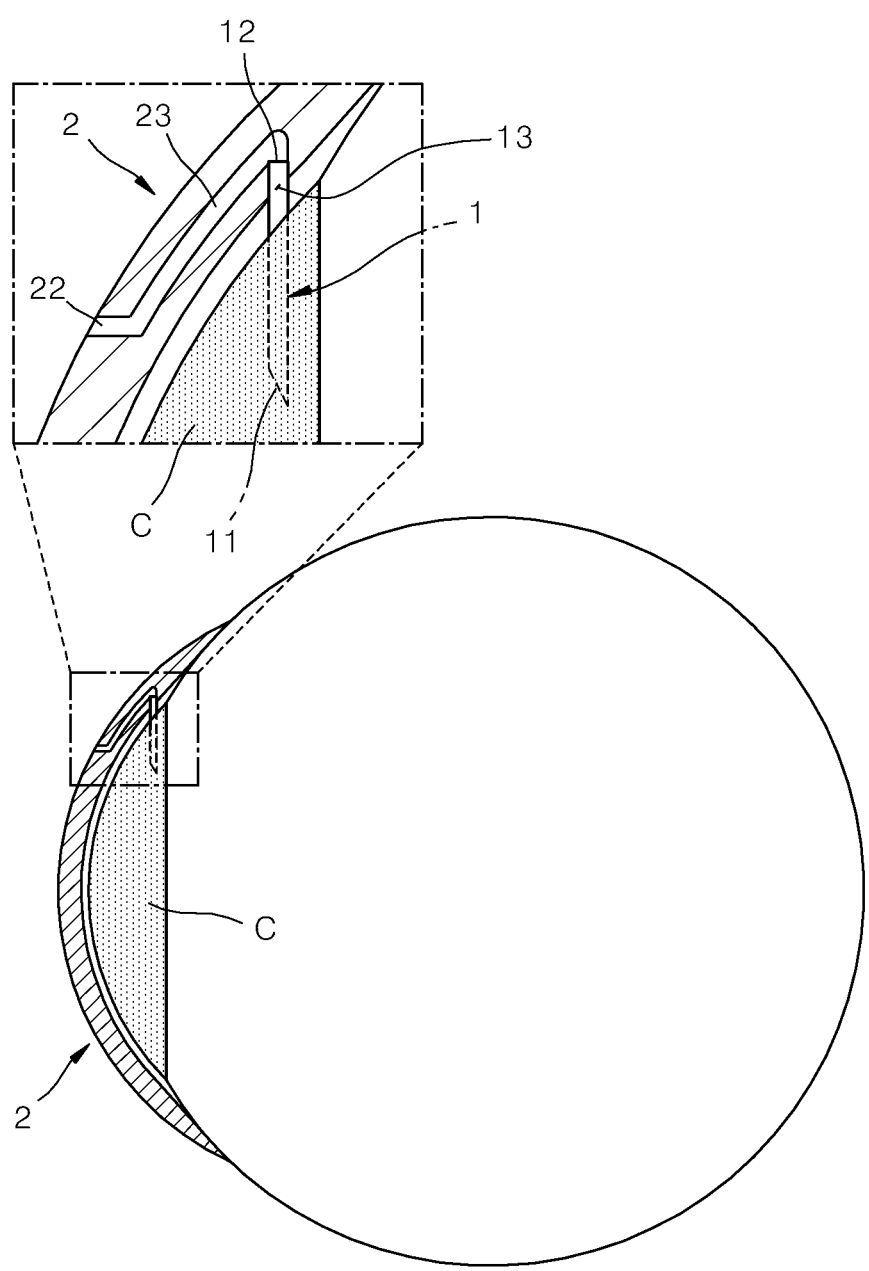
FIG. 5 is a cross-sectional view taken along line V-V of FIG. 4.

FIG. 3 is a cross-sectional view of the aqueous humour discharge apparatus for glaucoma prevention according to an embodiment of the present disclosure, FIG. 4 is a view illustrating a use state according to an embodiment of the present disclosure, and FIG. 5 is a cross-sectional view taken along line V-V of FIG. 4.

As shown in FIGS. 3 through 5, the aqueous humour discharge apparatus for glaucoma prevention according to an embodiment of the present disclosure is used to treat or prevent glaucoma, and includes an aqueous humour discharge tube 1 and a cover member 2.

The aqueous humour discharge tube 1 mainly contacts a cornea C surrounding the iris of an eyeball, in order to discharge aqueous humour from a portion corresponding to the iris. One side of the aqueous humour discharge tube 1 contacts the cornea C, and the other side thereof is exposed.

In other words, as shown in FIGS. 3 and 5, the aqueous humour discharge tube 1 is formed as a tube in which a channel 13 enabling the aqueous humour to flow is formed, a contact portion 11 that contacts the cornea C of the eyeball is provided on the one side of the aqueous humour discharge tube 1, and an exposed portion 12 exposed not in contact with the sclera of the eyeball and communicating with the contact portion 11 via the channel 13 is provided on the other side thereof.

The aqueous humour discharge tube 1 may be formed of a material that does not cause infection even when in long-time contact with the eyeball, like contact lenses. Not only the exposed portion 12 but also remaining portions except for the contact portion 11 may be arranged to be not in contact with the sclera. The aqueous humour discharge tube 1 may be detachably connected to the cover member 2 to facilitate infection treatment or replacement of the cover member 2.

As shown in FIGS. 4 and 5, the cover member 2 is arranged such that it surrounds the cornea C and the sclera, and thus protects the eyeball from external infection materials.

The cover member 2 includes a contact hole 21 formed on one side thereof that contacts the cornea C, a discharge hole 22 located on an opposite side to the one side and exposed, and a flow channel 23 provided between the contact hole 21 and the discharge hole 22. The contact hole 21 is a portion that the aqueous humour discharge tube 1 contacts and the discharge hole 22 is a portion that discharges the aqueous humour that has flowed into the flow channel 23 of the cover member 2 through the channel 13 of the aqueous humour discharge tube 1.

According to the present embodiment, the cover member 2 is configured to surround not only the cornea C but also the sclera including fiber cells, and thus the aqueous humour flowing through the aqueous humour discharge tube 1 is discharged via the cover member 2 without contacting the sclera. Therefore, a foreign body reaction does not occur, and accordingly fibrotic capsulation as a conventional problem does not occur.

As a result, the aqueous humour discharge apparatus for glaucoma prevention according to an embodiment of the present disclosure includes the aqueous humour discharge tube 1 contacting the cornea to discharge aqueous humour but not contacting the sclera, and the cover member 2 surrounding the cornea and the sclera and contacting the aqueous humour discharge tube 1 in order to discharge the aqueous humour forwards, as described above, thereby enabling the aqueous humour to be discharged through the cover member 2 while not in contact with the sclera. This addresses a conventional problem caused due to discharge of aqueous humour through the sclera, and thus it is possible to expect an excellent effect on the treatment or prevention of glaucoma through smooth discharge of aqueous humour and stabilization of the intraocular pressure.

According to the present embodiment, because the aqueous humour discharge tube 1 is in contact with the cornea and at this state the cover member 2 may be coupled with and separated from the aqueous humour discharge tube 1, the cover member 2 may be smoothly replaced and treatment, such as disinfection, of the aqueous humour discharge tube 1 may be smoothly performed, and thus the convenience of users and operators may improve.

Because the cover member 2 is formed as a contact lens by using a material as a contact lens material, inconvenience, infection, and the like may not occur even when the aqueous humour discharge apparatus for glaucoma prevention according to an embodiment of the present disclosure is worn on the eyeball for a long time. In particular, because a nano material that inhibits growth of bacteria is added when the cover member 2 is formed of a material as a contact lens material, antibiosis may be more increased.

Figure 6:
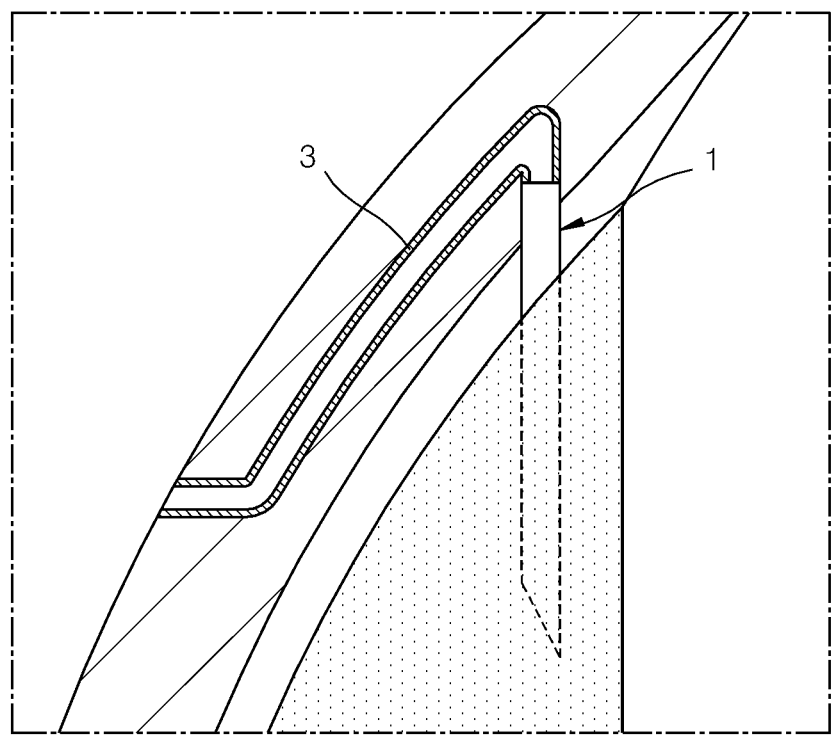
FIG. 6 is a cross-sectional view illustrating a structure of an aqueous humour discharge apparatus for glaucoma prevention according to another embodiment of the present disclosure.
Figure 7:
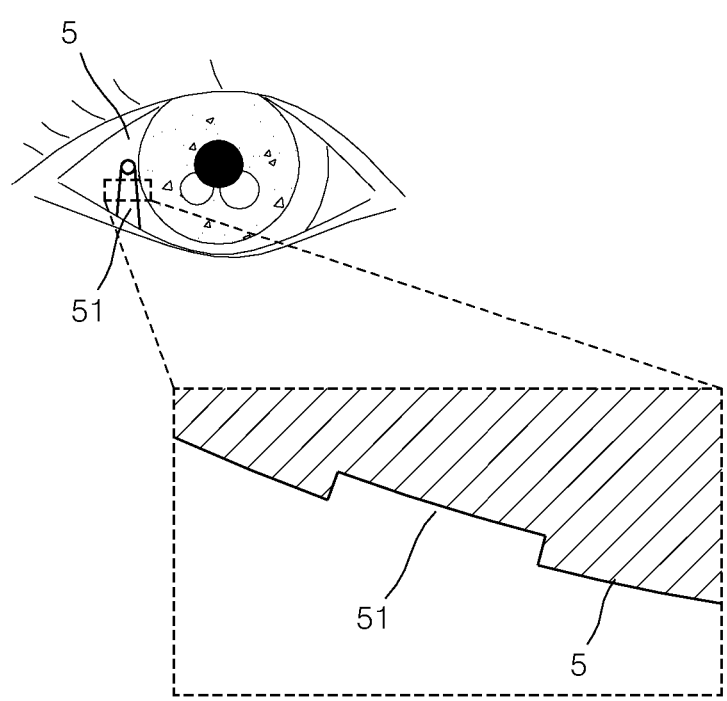
FIG. 7 is a use state view for explaining a schematic structure of an aqueous humour discharge apparatus for glaucoma prevention according to another embodiment of the present disclosure.

FIG. 6 is a cross-sectional view illustrating a structure of an aqueous humour discharge apparatus for glaucoma prevention according to another embodiment of the present disclosure.

In the present embodiment, in contrast with the previous embodiment where a flow channel of a cover member is formed by a channel integrally formed with the cover member, the flow channel of the cover member is formed by a flow channel formation member 3 formed together with the cover member according to an insert injection method when the cover member is molded.

The flow channel formation member 3 is formed of a more rigid material than a material of the cover member when the cover member is formed of a flexible material as a contact lens material, thereby enabling firm positioning within the cover member and smooth connection with the aqueous humour discharge tube 1.

In the above-described embodiments, the flow channel of the cover member is formed over a portion of the cornea. However, according to another embodiment of the present disclosure, the flow channel of the cover member may be located on the sclera instead of being located on the cornea, to prevent vision distortion or the like of a user.

FIG. 4 is a use state view for explaining a schematic structure of an aqueous humour discharge apparatus for glaucoma prevention according to another embodiment of the present disclosure.

According to the present embodiment, a guide channel 51 for discharging aqueous humour is formed on a cover member 5. In order to prevent aqueous humour having passed through a discharge hole of the cover member 5 from obstructing the vision, the guide channel 51 provides a discharge path of the aqueous humour.

Although various embodiments of the present disclosure have been described above, the present embodiments and the drawings attached to the present specification merely show a part of the technical spirit included in the present disclosure. It will be apparent that modifications and specific embodiments that can be easily inferred by those skilled in the art within the scope of the technical idea are included in the scope of the present disclosure.

The invention claimed is:

1. An aqueous humour discharge apparatus for glaucoma prevention, comprising:
   an aqueous humour discharge tube including a contact portion provided on one side of the aqueous humour discharge tube and contacting a cornea of an eyeball, an exposed portion exposed not to contact a sclera of the eyeball and provided on the other side the aqueous humour discharge tube, and a channel formed between the contact portion and the exposed portion to enable aqueous humour to flow therethrough; and
   a cover member arranged to surround the cornea and the sclera, the cover member including a contact hole formed on one surface that contacts the cornea and contacted by the aqueous humour discharge tube, a discharge hole formed on the other surface located at the opposite side to the one surface and exposed to an outside to discharge the aqueous humour, and a flow channel provided between the contact hole and the discharge hole to provide a discharge path of the aqueous humour.

2. The aqueous humour discharge apparatus for glaucoma prevention of claim 1, wherein the cover member is formed as a contact lens type by using a material that is the same as a material of a contact lens.

3. The aqueous humour discharge apparatus for glaucoma prevention of claim 1, wherein a flow channel formation member for forming the flow channel of the cover member is formed together with the cover member by an insert injection method when the cover member is molded, and the aqueous humour discharge tube is detachably combined with flow channel formation member.

4. The aqueous humour discharge apparatus for glaucoma prevention of claim 1, wherein the flow channel of the cover member is arranged at a location of the sclera without being located on the cornea.

\* \* \* \* \*